United States Patent [19]
Gellman

[11] Patent Number: 5,057,083
[45] Date of Patent: Oct. 15, 1991

[54] VASCULAR DILATOR WITH TRUNCATED TIP

[75] Inventor: Barry N. Gellman, Nashua, N.H.

[73] Assignee: C. R. Bard, Inc., Murray Hill, N.J.

[21] Appl. No.: 385,010

[22] Filed: Jul. 25, 1989

[51] Int. Cl.$^5$ ............................................ A61M 5/178
[52] U.S. Cl. ............................... 604/164; 604/280; 604/272
[58] Field of Search ............... 604/164, 272, 264, 280

[56] References Cited

U.S. PATENT DOCUMENTS

| | | | |
|---|---|---|---|
| 3,877,429 | 4/1975 | Rasumoff | 128/214.4 |
| 4,565,545 | 1/1986 | Suzuki | 604/164 |
| 4,588,398 | 5/1986 | Daugherty et al. | 604/265 |
| 4,617,019 | 10/1986 | Fecht et al. | 604/280 |
| 4,629,450 | 12/1986 | Suzuki et al. | 604/164 |
| 4,721,506 | 1/1988 | Teves | 604/164 X |
| 4,772,266 | 9/1988 | Groshong | 604/164 |
| 4,850,960 | 7/1989 | Grayzel | 604/280 X |
| 4,895,564 | 1/1990 | Farrell | 604/164 |
| 4,944,729 | 7/1990 | Buckberg et al. | 604/164 |

*Primary Examiner*—Robert Bahr
*Assistant Examiner*—J. Doyle
*Attorney, Agent, or Firm*—Wolf, Greenfield & Sacks

[57] ABSTRACT

A vascular dilator has a truncated tip adapted to reduce the risk of trauma to a blood vessel into which the dilator is to be inserted. The vascular dilator comprises an elongate tube having a guide member lumen of uniform diameter in which a guide member may pass. The thickness of the walls of the elongate tube decreases at the distal portion to create a tapered configuration. The distal portion terminates in an outlet defined by first and second arcuate segments. The first arcaute segment lies generally in a plane perpendicular to the longitudinal axis of the tube, whereas the second segment lies so as to meet the first segment at angle in the range of 30° to 60°.

11 Claims, 3 Drawing Sheets

VASCULAR DILATOR WITH TRUNCATED TIP

FIELD OF THE INVENTION

This invention relates to vascular dilators for dilating a needle puncture in a blood vessel in preparation for insertion of a larger diameter catheter into the blood vessel.

BACKGROUND OF THE INVENTION

Vascular dilators are commonly used when inserting a catheter into a blood vessel in order to widen the hole formed by the initial needle or scalpel puncture so that it is better able to receive the larger diameter catheter. The use of the dilator gradually enlarges the hole. In a typical procedure, a hollow needle is percutaneously inserted into the blood vessel and an elongate, slender guide member, such as a cannula or a guidewire is advanced through the hollow needle into the blood vessel. The needle then is removed over the guide member leaving the guide member in place in the blood vessel and extending proximally out of and through the patient's skin. The hole left by the needle in the blood vessel typically is too small to permit the catheter to be passed therethrough. A dilator is provided to widen the hole. Dilators commonly are in the form of a flexible plastic tube having a guide member lumen adapted to be passed over the guide member. The dilator is of uniform wall thickness except for a distal portion which tapers in a distal direction to the circular distal outlet opening at the distal end of the dilator. The wall thickness of the dilator at the distal tip is relatively thin to facilitate its entry into the hole made by the needle. As the dilator is advanced over the guide member through the puncture hole, the tapered distal portion presents a progressively wider diameter to the puncture hole, thus gradually enlarging the hole. The catheter may be mounted on and carried by the dilator so that once the dilator has been inserted to its full diameter into the blood vessel, the catheter then may be advanced over the dilator and through the enlarged puncture hole into the blood vessel. The dilator and guide member then may be withdrawn leaving the percutaneously placed catheter in place in the blood vessel.

Although there is a relatively close fit between the guide member and the circular opening defined by the distal tip of the dilator about the guide member, there necessarily is some clearance and it sometimes occurs that the intima of the blood vessel may become pinched or caught between the edge at the distal tip of the dilator and guide member. The blood vessel thus may become damaged, particularly if the pinching is unnoticed and the insertion of the dilator is continued. Therefore, there is a need for a dilator that reduces the risk of such traumatic injury to the blood vessel. It is among the general objects of the invention to provide an improved dilator that reduces the risk of pinching the blood vessel and reduces trauma to the blood vessel.

SUMMARY OF THE INVENTION

The dilator of the present invention has a plastic tubular sheath having a guide member lumen extending from its proximal to its distal end. The guide member lumen is of uniform diameter fully along its length. The distal end of the sheath has a tapered outer diameter and tapers to a thin wall. The clearance between the guide member and lumen of the sheath is relatively small, of the order of less than 0.01". The distal end of the lumen is truncated to lie generally along a plane that lies in an acute angle to the dilator axis and which intersects the general plane of the otherwise circular opening and the guide member lumen. The truncated portion meets the tissue of the blood vessel in a manner that enables the blood vessel tissue to slide onto the truncated portion without being pinched. The truncated portion overlies a projected area of the guide member lumen that is at least half of the projected area.

It is among the objects of the invention to provide an improved blood vessel dilator adapted to be passed over a guide member. A further object of the invention is to provide an improved blood vessel dilator that reduces the tendency for the blood vessel to become pinched between the guide member and the distal tip of the vessel dilator.

A further object of the invention is to provide a vessel dilator having a tip construction which facilitates smooth entry of the dilator into the blood vessel.

DESCRIPTION OF THE DRAWINGS

The foregoing and other objects and advantages of the invention will be appreciated more fully from the following further description thereof, with reference to the accompanying drawings wherein.

DESCRIPTION OF THE ILLUSTRATIVE EMBODIMENT

Figure 1:
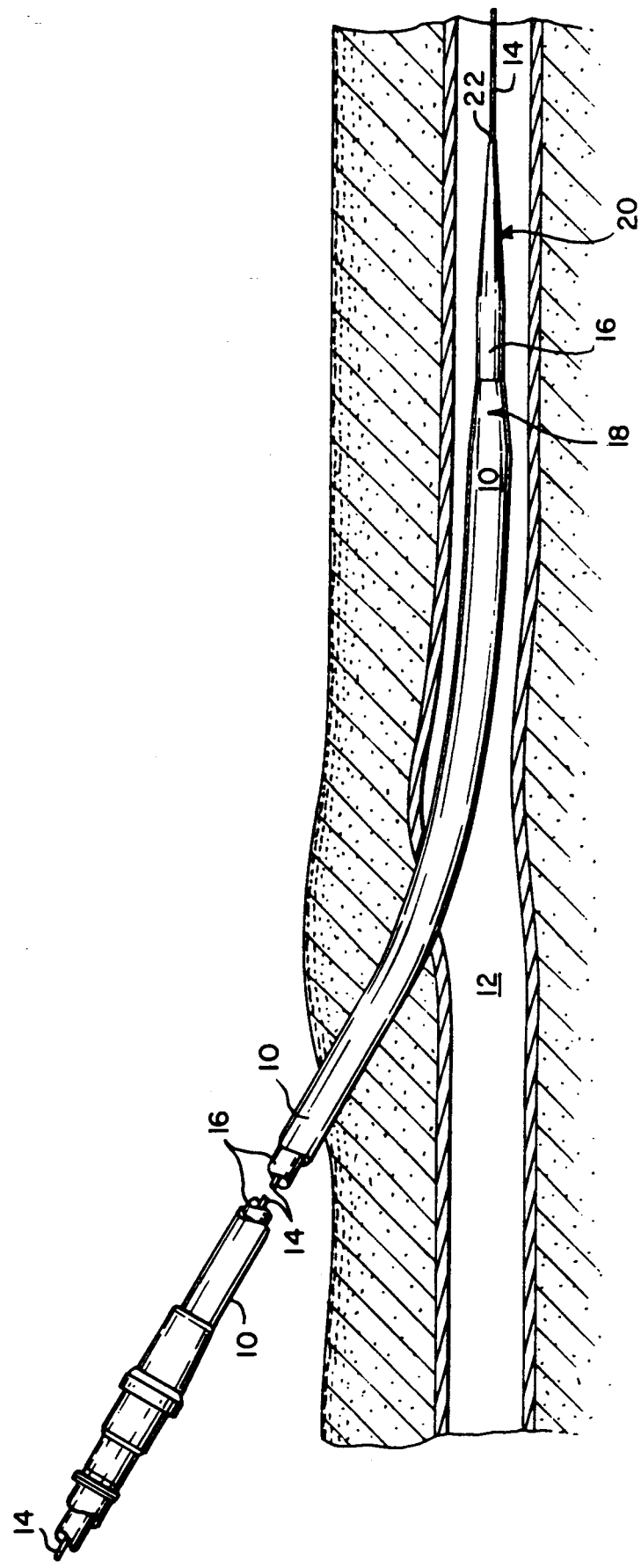
FIG. 1 is an illustration of a guide member, dilator and catheter percutaneously placed within a blood vessel.

FIG. 1 illustrates the manner in which a catheter 10 is inserted percutaneously into the blood vessel 12 of a patient using a guide member 14 and a dilator 16. In the illustrations and following description, the guide member 14 is illustrated as being a guidewire, although it should be understood that any elongate flexible guiding member may be employed such as a cannula or wire element or other suitable synthetic material which may be coated with or formed from a lubricious material. The procedure typically involves an initial needle puncture with a hollow needle (not shown) that is inserted through the patient's skin into the blood vessel. The distal end of the guide member 14 then is passed through the hollow needle into the patient s blood vessel. The needle then is withdrawn over the proximal end of the guide member 14. The catheter 10 typically will be carried on the dilator 16 which passes through the lumen of the catheter 10 and projects distally beyond the distal end 18 of the catheter 10. The distal portion 20 of the dilator 16 is tapered so that the wall thickness of the dilator at its distal tip 22 is thinner than in the more proximal portions of the dilator and will present a relatively smooth transition from the guide member to the dilator as the dilator advances through the wall of the blood vessel. The dilator is advanced to progressively widen the opening in the blood vessel Once the full diameter of the dilator has been inserted into the blood vessel, the catheter then may be advanced into the blood vessel, the dilation having widened the hole to facilitate entry of the larger diameter catheter. Once the catheter 10 has been inserted into the blood vessel 12, the guide member 14 and dilator 16 are removed, leaving the catheter in place in the blood vessel to perform its intended function.

The dilator typically is formed from a lubricious plastic material such as polytetrafluoroethylene or polyethylene to provide a high degree of lubricity in the blood vessel as well as with respect to movement of the catheter over the dilator 16. The dilator typically is provided with a hub at its proximal end and is of a length slightly greater than the length of the catheter assembly so that when the hub of the dilator is advanced fully distally against the proximal end of the catheter assembly, the distal portion 20 of the dilator will project beyond the distal end of the catheter. Thus, the length of the dilator will depend on the length of the catheter.

Figure 2:
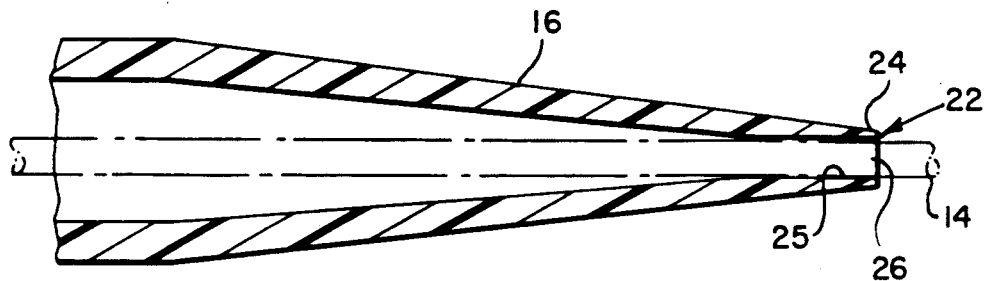
FIG. 2 is an enlarged cross-sectional illustration of a typical dilator of the prior art which is in common use.
Figure 3:
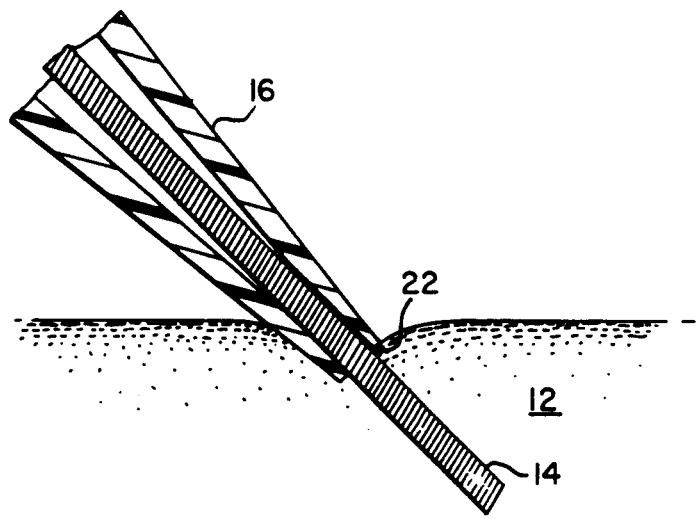
FIG. 3 is an illustration of the prior art dilator of FIG. 2 showing the manner in which it may tend to pinch the blood vessel.

FIG. 2 illustrates in enlarged detail the distal tip of a conventional dilator in relation to a guide member 14. Although the wall of the dilator is progressively thinner in a distal direction, it nevertheless terminates in a blunt annular face 24. Typically, the annular face 24 may define a terminal wall thickness of the order of up to 0.01". Additionally, there is a slight clearance between the lumen 26 of the dilator 16 and the guide member 14. Typically, the slight clearance at the distal tip of the dilator 16 is defined by an annular cylindrical, untapered surface 25. As shown in FIG. 3, when such a conventional dilator 16 is advanced over the guide member 14 into the blood vessel 12, it may catch and pinch the wall or a portion of the wall of the blood vessel, such as the delicate intimal lining, in the annular clearance between the guide member 14 and dilator tip 22. Should the blood vessel become caught, it may not be noticed and further advancement of the dilator into the blood vessel may cause injury to the blood vessel.

Figure 4:
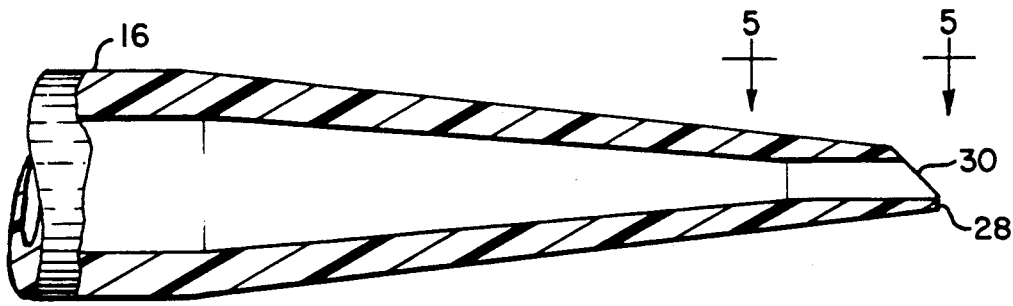
FIG. 4 is a side elevation of the tip construction of the dilator in accordance with the invention.
Figure 5:
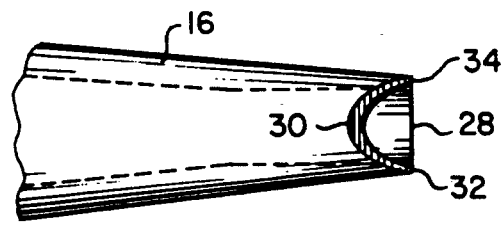
FIG. 5 is an illustration of the tip construction of the invention as seen from the line 5—5 of FIG. 4 (top view)
Figure 6:
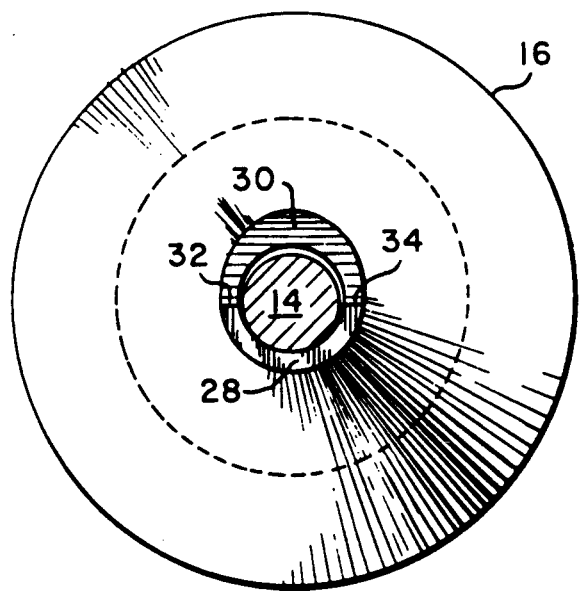
FIG. 6 is an end view of the dilator as seen from the left of FIG. 4.

FIGS. 4–6 illustrate the improved dilator of the present invention. In accordance with the invention, the distal tip of the dilator is formed with a truncated segment that lies generally along a plane that intersects the plane of the otherwise generally circular opening. More particularly, the distal tip of the present invention may be considered as having an edge defined by a first arcuate, such as partially circular segment 28 that lies generally in a plane perpendicular to the longitudinal axis of the dilator 16 and a second arcuate segment 30 that extends from one end of the first arcuate, such as partially circular segments 28, at a junction 32, to the other end of the first arcuate, such as partially circular segment 28 at a junction 34. Preferably, the second arcuate segment lies generally in a plane that meets the plane of the first arcuate, such as partially circular segment 28 at an angle A of between approximately 30° to 60°. The second arcuate segment preferably is planar although it could be provided with somewhat of a curved configuration, it not being strictly essential that the segment be perfectly planar. In the preferred embodiment, the junctures 32, 34 define a chord (as seen from a projected end view such as FIG. 6) with the area circumscribed by the chord and the first arcuate, such as partially circular segment 28 being no greater than one-half the axially projected area of the lumen. Thus, the arcuate, such as partially circular segment 28 preferably defines an arc not substantially greater than about 180° and may define an arc less than 180°. Thus, the second arcuate segment 30 defines an axially projected arc that is at least equal to about 180°. It should be understood that the juncture 32, 34 and the outermost edge of segment 28 may be rounded and need not be geometrically sharp points. The inner surface, 35, at the distal end of the guide member lumen of the dilator 16 preferably is untapered to define a generally cylindrical configuration.

Figure 7:
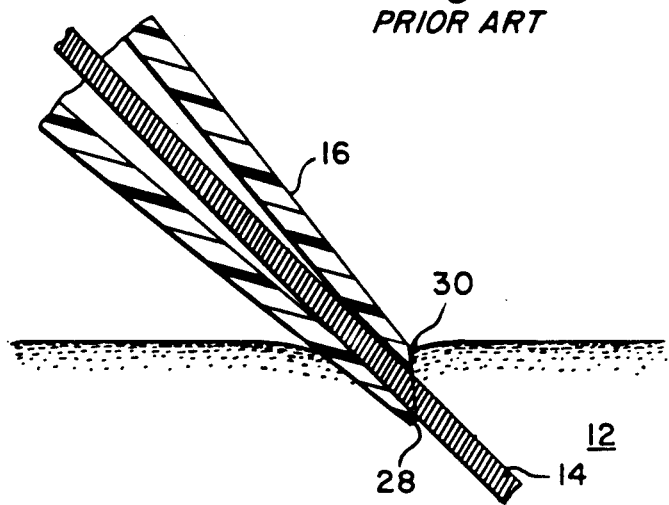
FIG. 7 is an illustration of the dilator of the invention being inserted into a blood vessel.

FIG. 7 illustrates the manner in which the dilator of the present invention enters the puncture hole of an artery. The needle typically is inserted at an acute angle to the artery and the guide member extends at such an angle into the artery so that it will guide the dilator into the artery at such angle. As illustrated in FIG. 7, it can be seen that the first arcuate, such as partially circular segment 28 initially contacts the outer surface of the blood vessel 12 and pushes it down and out of the way so that it advancement will not bluntly engage any portion of the blood vessel. As the first arcuate, such as partially circular segment 28 begins the enlargement of the needle hole, the hole widens until the junctures 32, 34 have reached the blood vessel wall. The blood vessel wall then rides up onto the second arcuate segment 30 so that continued advancement of the dilator causes the blood vessel wall to ride smoothly over the second arcuate segment, thus progressively enlarging the hole without risk of pinching the intimal lining of the blood vessel During insertion, it may be desirable to impart a slight rotational motion to the dilator simultaneously as is advanced axially.

From the foregoing, it will be appreciated that the present invention provides an improved dilator construction and method for dilating a blood vessel during wire or similarly guided insertion of a catheter. It should be understood, however, that the foregoing description of the invention is intended merely to be illustrative thereof and that other embodiments and modifications may be apparent to those skilled in the art without departing from its spirit.

Having thus described the invention, what I desire to claim and secure by letters patent is:

1. A vascular dilator for use with a guide member comprising:
   an elongate tube having a uniform inner diameter defining a guide member lumen;
   the dilator having a distal portion with a distally reducing wall thickness to define a tapered configuration, the distal portion terminating in an outlet with an edge having a first arcuate segment portion that lies generally in a plane perpendicular to the longitudinal axis of the tube and a second arcuate segment that extends from one end of the first segment to the other end of the first segment, said segments meeting at an angle that lies in the range of between about 30° to about 60°.

2. A vascular dilator as defined in claim 1 wherein a chord line extending between the junctures of the segments intersects a projection of the guide member lumen so that the area circumscribed by the chord line and the first arcuate segment is no more than one-half of the projected area of the lumen.

3. A vascular dilator as defined in claim 2 wherein the juncture of the segments lie on points that intersect the diameter of a circle that is partly defined by the first arcuate segment.

4. A dilator as defined in claim 2 wherein said area is less than one-half of the lumen.

5. A vascular dilator as defined in claim 1 wherein said first arcuate segment defines an arc no greater than about 180°.

6. A vascular dilator as defined in claim 1 wherein said second arcuate segment defines an axially projected arc of at least about 180°.

7. A dilator as defined in any of claims 1-6 further comprising, in combination, said guide member, said guide member extending through the lumen of the dilator.

8. A dilator as defined in any of claims 1-6 further comprising, in combination, said guide member and a catheter, the guide member extending through the lumen of the dilator and the catheter being mounted on the dilator.

9. A vaculator dilator as defined in claim 1 wherein the first arcuate segment lies in a circle in the plane perpendicular to the longitudinal axis of the tube, said circle being centered at the longitudinal axis of the tube and having a radius extending from the longitudinal axis of the tube to the first arcuate segment.

10. A method for dilating a blood vessel comprising:
percutaneously inserting a guide member into the blood vessel of a patient; and providing a dilator as defined in any one of claims 1-6; and advancing the dilator over the guide member into the blood vessel until the second arcuate segment reaches a wall of blood vessel so that the first arcuate segment engages and displaces an outer surface of the blood vessel so that further advancement of the dilator does not bluntly engage the outer surface of vessel;

further advancing the dilator over the guide member into the blood vessel so that the wall of the blood vessel rides over the second arcuate segment without harming the blood vessel.

11. A method as defined in claim 10 further comprising rotating the dilator while inserting it into the vessel.

* * * * *